(12) United States Patent
Janzig et al.

(10) Patent No.: US 11,872,392 B2
(45) Date of Patent: *Jan. 16, 2024

(54) DIFFUSION BONDED LEAD CONNECTOR

(71) Applicant: Medtronic, Inc., Minneapolis, MN (US)

(72) Inventors: Darren A. Janzig, Center City, MN (US); Andrew J. Thom, Maple Grove, MN (US); Chris J. Paidosh, St. Anthony, MN (US); Brad C. Tischendorf, Minneapolis, MN (US); Gerald G. Lindner, Lino Lakes, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/536,360

(22) Filed: Nov. 29, 2021

(65) Prior Publication Data

US 2022/0080188 A1 Mar. 17, 2022

Related U.S. Application Data

(63) Continuation of application No. 15/363,178, filed on Nov. 29, 2016, now Pat. No. 11,213,673, which is a
(Continued)

(51) Int. Cl.
*A61N 1/05* (2006.01)
*H01R 13/187* (2006.01)
(Continued)

(52) U.S. Cl.
CPC ............. *A61N 1/05* (2013.01); *A61N 1/3752* (2013.01); *B23K 20/026* (2013.01); *B23K 26/21* (2015.10); *C23C 14/10* (2013.01); *C23C 14/18* (2013.01); *C23C 14/34* (2013.01); *H01R 13/187* (2013.01); *H01R 24/58* (2013.01); *H01R 43/0221* (2013.01); *A61B 2562/227* (2013.01); *B23K 2101/38* (2018.08); *B23K 2103/172* (2018.08);
(Continued)

(58) Field of Classification Search
CPC ................................ A61N 1/05; A61N 1/3752
See application file for complete search history.

(56) References Cited

U.S. PATENT DOCUMENTS 4,156,429 A * 5/1979 Amundson .......... A61N 1/0565
607/121
4,641,334 A * 2/1987 Devine, Jr. ........... H01J 35/108
378/127
(Continued)

OTHER PUBLICATIONS

Akelsen, Review Diffusion Bonding of Ceramics, The Welding Centre, The Foundation for Scientific and Industrial Research, Norwegian Institute of Technology, Journal of Materials Science 27, 1992, pp. 569-579.
(Continued)

*Primary Examiner* — Eric D. Bertram
(74) *Attorney, Agent, or Firm* — Mueting Raasch Group

(57) ABSTRACT

A medical device lead connector includes electrically conducting contact rings spaced apart by an electrically insulating ring and in axial alignment. The electrically conducting contact ring and the insulating ring having an interface bond on an atomic level.

17 Claims, 7 Drawing Sheets

Related U.S. Application Data continuation of application No. 13/088,913, filed on Apr. 18, 2011, now abandoned.

(60) Provisional application No. 61/329,260, filed on Apr. 29, 2010.

(51) Int. Cl.
| | | |
|---|---|---|
| *H01R 24/58* | (2011.01) | |
| *A61N 1/375* | (2006.01) | |
| *B23K 26/21* | (2014.01) | |
| *B23K 20/02* | (2006.01) | |
| *C23C 14/10* | (2006.01) | |
| *C23C 14/18* | (2006.01) | |
| *C23C 14/34* | (2006.01) | |
| *H01R 43/02* | (2006.01) | |
| *B23K 101/38* | (2006.01) | |
| *B23K 103/00* | (2006.01) | |
| *B23K 103/16* | (2006.01) | |
| *H01R 107/00* | (2006.01) | |

(52) U.S. Cl.
CPC ...... *B23K 2103/52* (2018.08); *B23K 2103/54* (2018.08); *H01R 2107/00* (2013.01); *H01R 2201/12* (2013.01); *Y10T 156/10* (2015.01)

(56) References Cited

U.S. PATENT DOCUMENTS

| | | | | |
|---|---|---|---|---|
| 5,496,359 | A  * | 3/1996 | Davidson | A61F 2/0077 |
| | | | | 607/115 |
| 6,174,329 | B1 * | 1/2001 | Callol | A61F 2/91 |
| | | | | 606/198 |
| 11,213,673 | B2 * | 1/2022 | Janzig | C23C 14/10 |
| 2007/0250158 | A1 * | 10/2007 | Krivoruchko | A61L 31/082 |
| | | | | 623/1.44 |
| 2008/0208278 | A1 * | 8/2008 | Janzig | H01R 43/16 |
| | | | | 607/37 |
| 2010/0109958 | A1 * | 5/2010 | Haubrich | A61N 1/37229 |
| | | | | 343/718 |
| 2010/0179627 | A1 * | 7/2010 | Floyd | H01R 4/20 |
| | | | | 607/116 |
| 2011/0270330 | A1 * | 11/2011 | Janzig | B23K 26/21 |
| | | | | 156/60 |

OTHER PUBLICATIONS

Gab et al., Metal-to-Sapphire Brazed and Diffusion Bonded Windows for Optics, Ultra-High Vacuum Technics and Electronics for Maintenance at Temperatures 77-800K, Institute for Problems of Materials Science of National Academy of Sciences of Ukraine, Proc. Int. Conf. High Temperature Capillarity, Jun. 29-Jul. 2, 1997, 6 pages.

* cited by examiner

DIFFUSION BONDED LEAD CONNECTOR

The present application is a continuation of U.S. patent application Ser. No. 15/363,178, filed Nov. 29, 2016, now U.S. Pat. No. 11,213,673 which is a continuation of U.S. patent application Ser. No. 13/088,913, filed Apr. 18, 2011, now abandoned, which claims priority to U.S. Provisional Patent Application No. 61/329,260, filed Apr. 29, 2010, which are hereby incorporated by reference in their entireties.

BACKGROUND

Implantable active medical devices, such as cardiac rhythm management devices (pacemakers and defibrillators) and a variety of implantable muscle/nerve stimulators, for example, generally include a battery and battery-powered electronic pulse generator contained within a hermetically sealed housing or case and attached to a lead connector housing or block. The lead connector block is often affixed to the hermetically sealed housing with brackets, and/or a medical grade adhesive.

The electronics within the hermetically sealed housing are conductively coupled to the lead connector block with an electrical feedthrough assembly. Electrical feedthroughs serve the purpose of providing a conductive path extending between the interior of a hermetically sealed container and a point outside the hermetically sealed housing. The conductive path through the feedthrough usually includes a conductor pin or terminal that is electrically insulated from the hermetically sealed housing. Many such feedthroughs are known in the art that provide the conductive path and seal the electrical container from its ambient environment. Such feedthroughs typically include a ferrule, and an insulative material such as a hermetic glass or ceramic seal that positions and insulates the pin within the ferrule. Sometimes it is desired that the electrical device includes a capacitor within the ferrule and around the terminal, thus shunting any electromagnetic interference (EMI) at high frequencies at the entrance to the electrical device to which the feedthrough device is attached. Typically, the capacitor electrically contacts the pin lead and the ferrule. While this arrangement has proven to be highly reliable, it involves a variety of expensive manufacturing processes and parts that necessarily increase the cost of the resulting product and increases the number of interconnects.

Ongoing efforts by the industry to reduce the size of the implantable device are desired. With advances in microelectronics and integrated circuitry, significantly more features and capabilities have been embodied in implantable active medical devices capable of sizes as small as about 10 cc. Nonetheless, efforts to further reduce the size of implantable active medical devices continue in the industry.

BRIEF SUMMARY

The present disclosure relates to diffusion bonded lead connectors. In particular the present disclosure relates to hermetic lead connectors that have contact portions separated by an insulating ring and joined together with an interface bond on an atomic level. The interface bond on an atomic level can be a solid state diffusion bond (i.e., diffusion bond) that forms a hermetic bond with the electrically insulating portions and electrically conducting contact portions of the hermetic lead connectors.

In one illustrative embodiment, a medical device lead connector includes electrically conducting contact rings spaced apart by an electrically insulating ring and in axial alignment. The electrically conducting contact ring and the insulating ring having an interface bond on an atomic level.

In another illustrative embodiment, an implantable medical device includes a hermetically sealed housing defining a sealed housing interior, a power source and electronics in electrical communication with and disposed within the sealed housing interior, and a lead connector projecting into the sealed housing interior. The lead connector has an outer surface, and an inner surface defining a lead aperture. The lead connector includes one or more electrically conducting contact rings spaced apart by electrically insulating rings and joined together with a diffusion bond. The one or more electrically conducting contact rings are in electrical communication with the electronics. The diffusion bond provides a hermetic seal between the lead connector outer surface and the lead connector inner surface.

In a further embodiment, a method of forming a medical device lead connector includes diffusion bonding an electrically insulating ring between a first electrically conducting contact ring and a second electrically conducting contact ring to form a joined element and then joining a plurality of joined elements in axial alignment to form a lead connector.

These and various other features and advantages will be apparent from a reading of the following detailed description.

BRIEF DESCRIPTION OF THE DRAWINGS

The disclosure may be more completely understood in consideration of the following detailed description of various embodiments of the disclosure in connection with the accompanying drawings, in which.

The figures are not necessarily to scale. Like numbers used in the figures refer to like components. However, it will be understood that the use of a number to refer to a component in a given figure is not intended to limit the component in another figure labeled with the same number.

DETAILED DESCRIPTION

Figure 1:
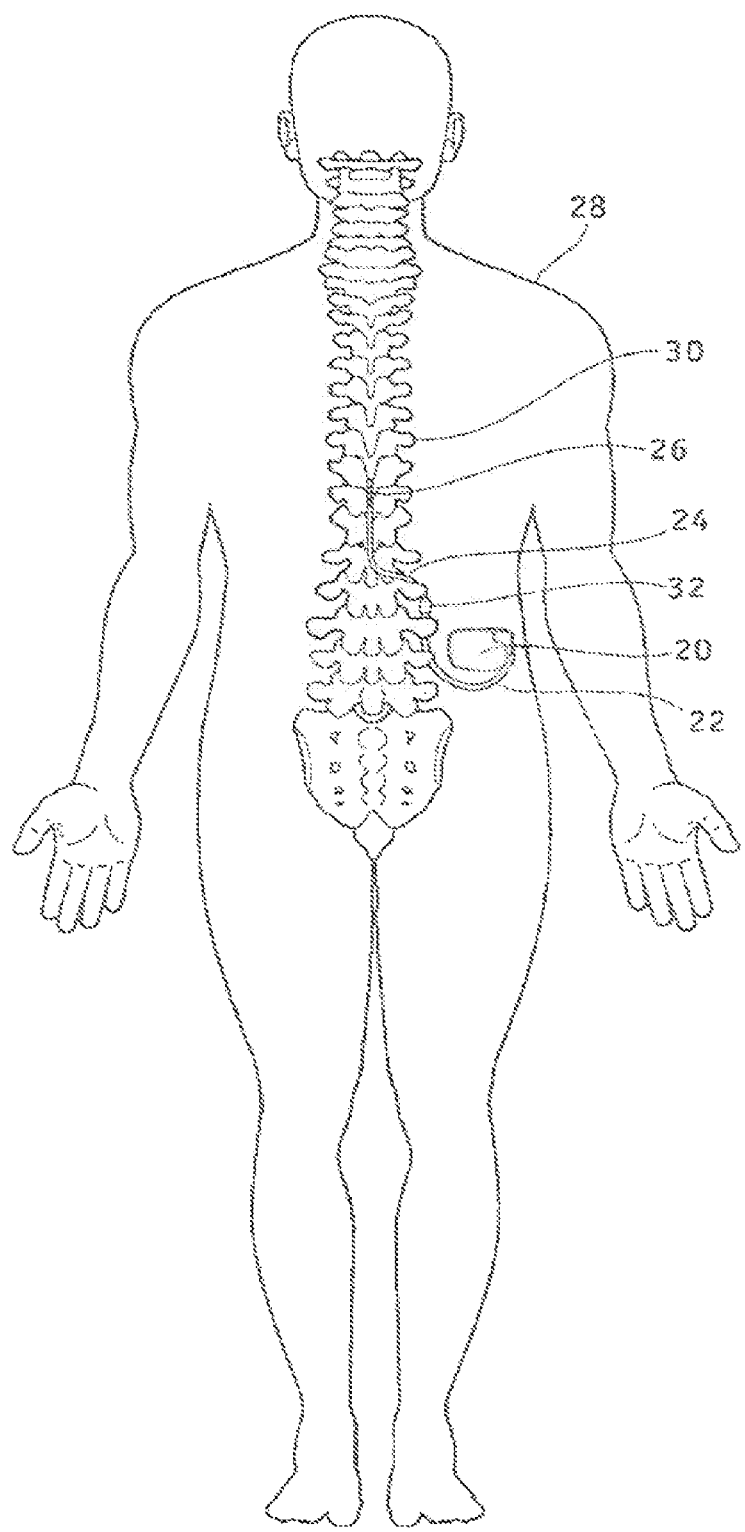
FIG. 1 is a schematic diagram of a an active medical device implanted within a human body.

In the following description, reference is made to the accompanying set of drawings that form a part hereof and in which are shown by way of illustration several specific embodiments. It is to be understood that other embodiments are contemplated and may be made without departing from the scope or spirit of the present disclosure. The following detailed description, therefore, is not to be taken in a limiting sense.

Unless otherwise indicated, all numbers expressing feature sizes, amounts, and physical properties used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings disclosed herein.

As used in this specification and the appended claims, the singular forms "a", "an", and "the" encompass embodiments having plural referents, unless the content clearly dictates otherwise. As used in this specification and the appended claims, the term "or" is generally employed in its sense including "and/or" unless the content clearly dictates otherwise.

Spatially related terms, including but not limited to, "lower", "upper", "beneath", "below", "above", and "on top", if used herein, are utilized for ease of description to describe spatial relationships of an element(s) to another. Such spatially related terms encompass different orientations of the device in use or operation in addition to the particular orientations depicted in the figures and described herein. For example, if an element depicted in the figures is turned over or flipped over, portions previously described as below or beneath other elements would then be above those other elements.

As used herein, when an element, component or layer for example is described as being "on" "connected to", "coupled with" or "in contact with" another element, component or layer, it can be directly on, directly connected to, directly coupled with, in direct contact with, or intervening elements, components or layers may be on, connected, coupled or in contact with the particular element, component or layer, for example. When an element, component or layer for example is referred to as begin "directly on", "directly connected to", "directly coupled with", or "directly in contact with" another element, there are no intervening elements, components or layers for example.

The present disclosure relates to hermetic diffusion bonded lead connectors. In particular the present disclosure relates to hermetic lead connectors that have electrically conducting contact portions separated by electrically insulating portions and diffusion bonded together. The diffusion bond forms a hermetic bond with the electrically conducting contact portions and the electrically insulating portions of the hermetic lead connectors. The diffusion bond eliminates gold or metal brazing material from the hermetic lead connector and thus the manufacturing temperatures of the hermetic lead connector is reduced, in many embodiments, to less than 1000 degrees centigrade. In addition, the diffusion bond allows the electrically conducting contact portions of the hermetic lead connector to be closer than has been conventionally available. For example, the pitch between electrical contact portions can be reduced to 0.085 inch or less. Utilizing diffusion bonding provides a number of advantages such as reducing the manufacturing temperature and reducing the size of the hermetic lead connectors, for example. While the present disclosure is not so limited, an appreciation of various aspects of the disclosure will be gained through a discussion of the examples provided below.

FIG. 1 is a schematic diagram of an active medical device 20 implanted within a human body or patient 28. The implanted active medical device 20 is illustrated as a neurostimulator, however, the implanted active medical device 20 can be any "active implantable medical device" or "implantable signal generator" as described above and can be placed in any location within a body cavity or tissue within the body, or on the surface of a patient's skin, as desired. In some embodiments the device is a non-active implantable medical device such as a sensor, for example.

The active medical device 20 is coupled to a lead extension 22 having a proximal end coupled to the active medical device 20, and a lead 24 having a proximal end coupled to a distal end 32 of the lead extension 22 and a distal end of the lead 24 coupled to one or more electrodes 26. In other embodiments, the lead 24 proximal end is coupled to the active medical device 20, without a need for a lead extension 22. The active medical device 20 can be implanted in any useful region of the body such as in the abdomen of a patient 28, and the lead 24 is shown placed somewhere along the spinal cord 30. In many embodiments, the active medical device 20 has one or two leads each having four to eight electrodes. Such a system may also include a physician programmer and a patient programmer (not shown). The active medical device 20 can be considered to be an implantable signal generator of the type available from Medtronic, Inc. and capable of generating multiple signals occurring either simultaneously or one signal shifting in time with respect to the other, and having independently varying amplitudes and signal widths. The active medical device 20 contains a power source and the electronics for sending precise, electrical signals to the patient to provide the desired treatment therapy. While the active medical device 20, in many embodiments, provides electrical stimulation by way of signals, other forms of stimulation may be used as continuous electrical stimulation.

In many embodiments, the lead 24 is a wire having insulation thereon and includes one or more insulated electrical conductors each coupled at their proximal end to a connector and to contacts/electrodes 26 at its distal end. Some leads are designed to be inserted into a patient percutaneously (e.g. the Model 3487A Pisces-Quad® lead available from Medtronic, Inc.), and some are designed to be surgically implanted (e.g. Model 3998 Specify® lead, also available from Medtronic, Inc.). In some embodiments, the lead 24 may contain a paddle at its distal end for housing electrodes 26. In many embodiments, electrodes 26 may include one or more ring contacts at the distal end of lead 24.

Figure 2:
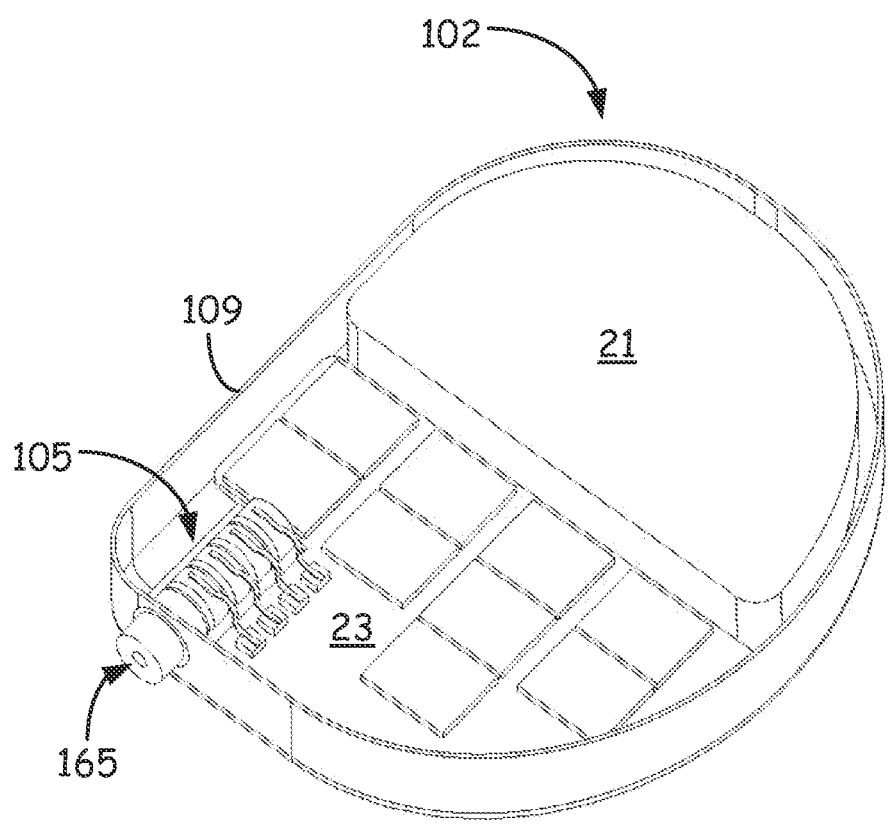
FIG. 2 is a schematic perspective view of an implantable active medical device with an internal hermetic lead connector.
Figure 3:
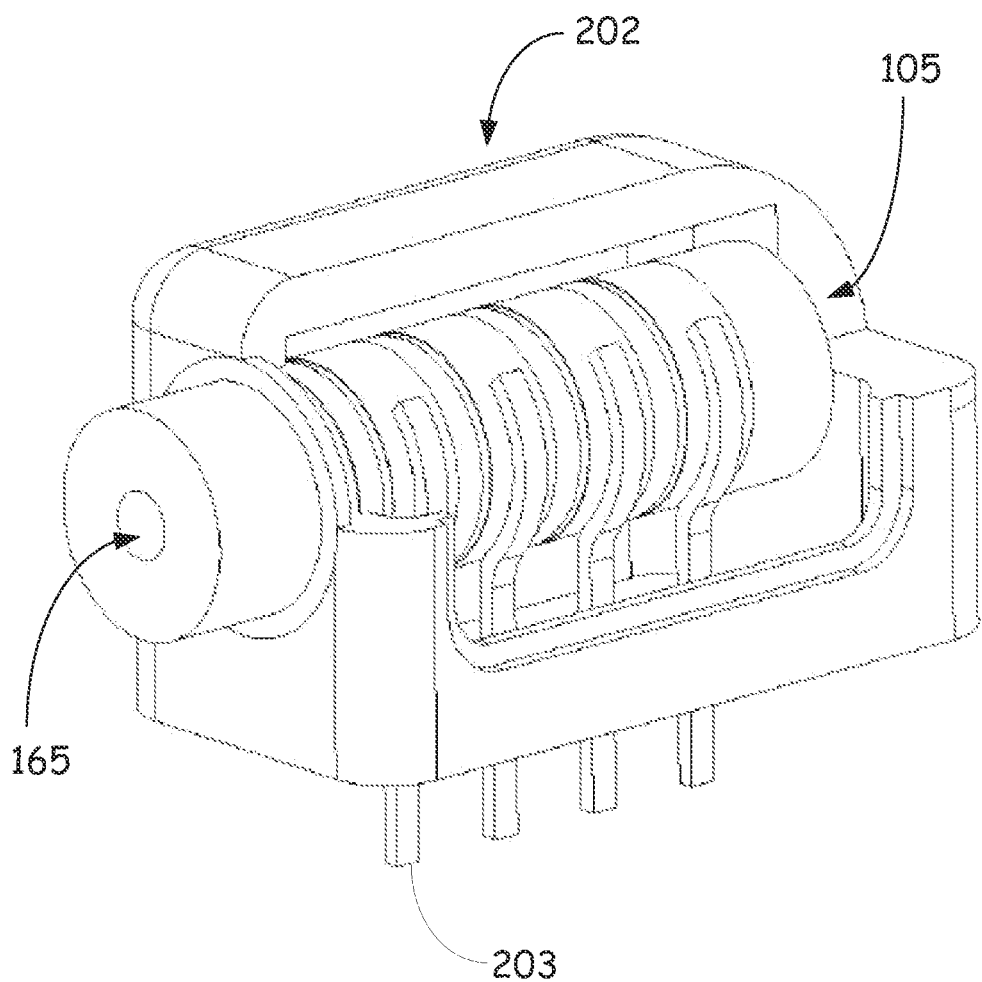
FIG. 3 is a schematic perspective view of an illustrative lead connector with an external lead connector.

FIG. 2 is a schematic perspective view of an implantable active medical device 102. FIG. 3 is a schematic cut-away perspective view of an implantable active medical device header 202 with an external hermetic lead connector. Thus the disclosed lead connector 105 can be utilized in a conventional device that relies on a feedthrough 203 to provide the hermetic barrier (see FIG. 3) or the disclosed lead connector 105 can be utilized to provide the hermetic barrier extending into a device (see FIG. 2). FIG. 3 does not show the hermetic enclosure for the electronics and power source, but it is understood that the hermetic enclosure would be adjacent to the feedthrough 203. FIG. 3 does not rely on the disclosed lead connector 105 to provide the device hermetic barrier, however the disclosed lead connector 105 provides a rigid lead connector with electrical contacts at a fixed pitch.

The active medical device 102 includes a hermetically sealed housing 109 defining a sealed housing interior. The active medical device 102 is illustrated without a cover portion that would complete the hermetic sealed housing 109. A power source 21 and electronics 23 are in electrical communication and are disposed within the sealed housing 109 interior. A lead connector 105 projects into and through the sealed housing 109 interior and has an inner surface or lead receptacle defining an open lumen lead aperture 165. In many embodiments an outer surface of the lead connector 105 at least partially defines the sealed housing interior surface.

A "diffusion bond" refers to technique of bonding materials in the solid state to form a monolithic joint through the formation of bonds at an atomic level, as a result of closure of the mating surfaces due to the local plastic deformation at elevated pressure and temperature which aids interdiffusion at the surface layers of the materials being joined. Solid-state diffusion bonding is a process by which two nominally flat interfaces can be joined at an elevated temperature (about 50 to 90% of the absolute melting point of the parent material) using an applied pressure for a time ranging from a few minutes to a few hours. Joining of dissimilar materials with different thermo-physical characteristics, which is not possible by other processes, may be achieved by diffusion bonding. Metal, alloys, ceramics and powder metallurgy products can be joined by diffusion bonding. A diffusion bond forms a hermetic seal.

Figure 4:
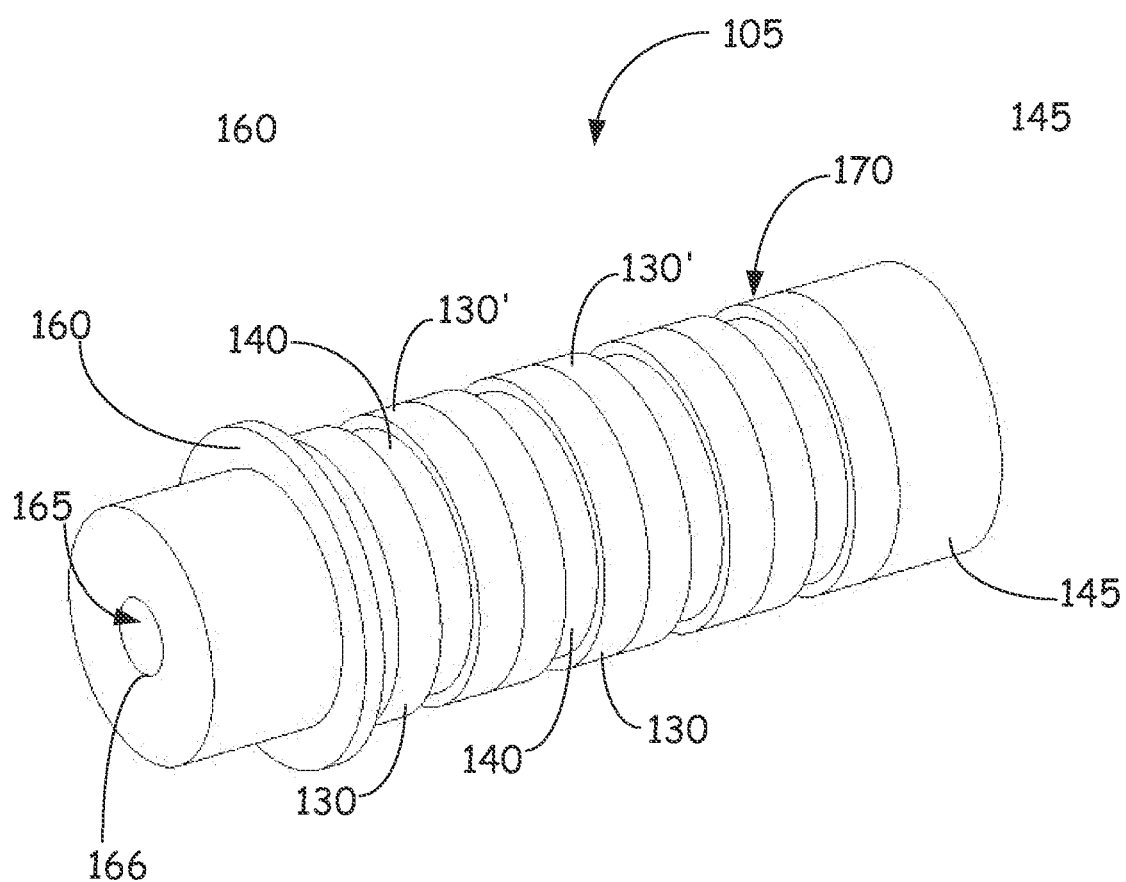
FIG. 4 is a perspective schematic diagram view of an illustrative lead connector.
Figure 5:
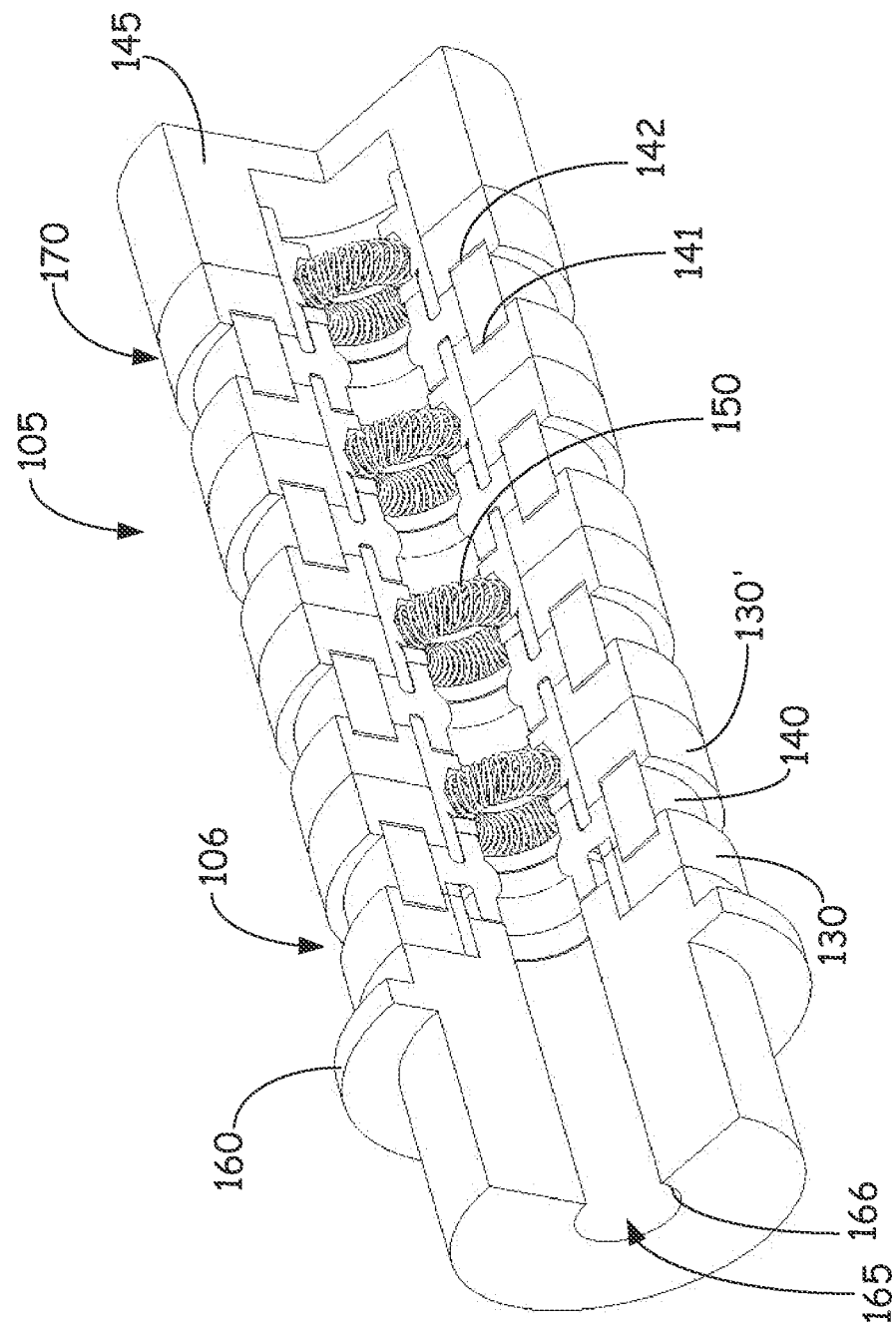
FIG. 5 is an perspective cut-away view of the illustrative lead connector shown in FIG. 4.
Figure 6:
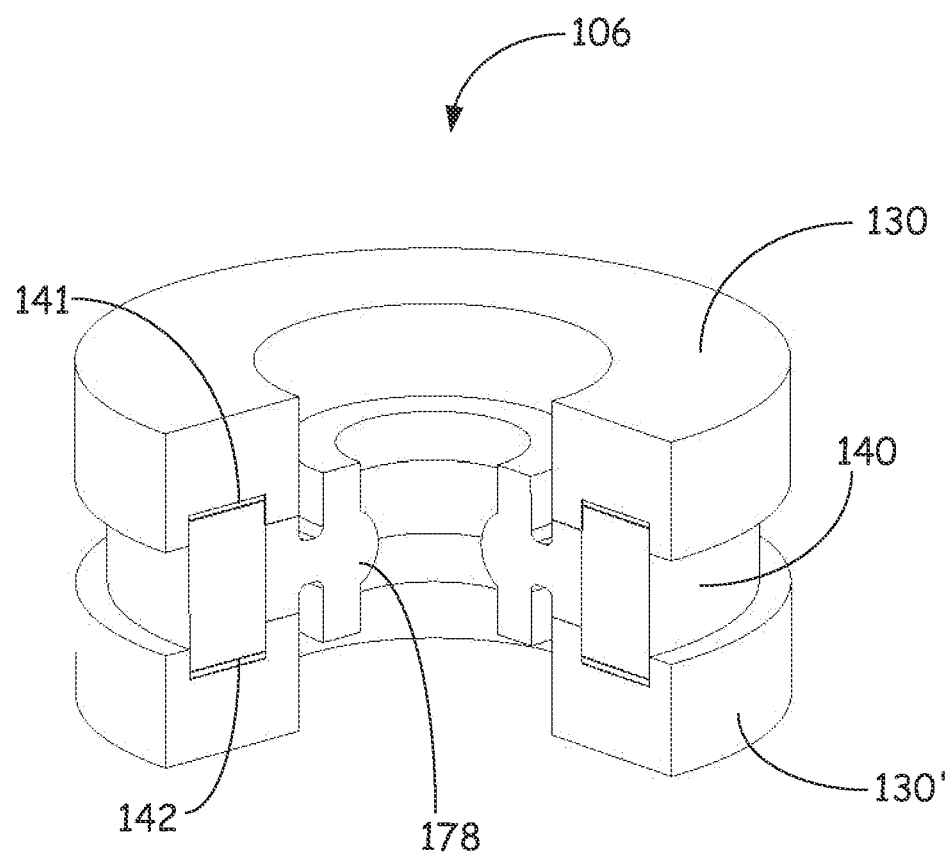
FIG. 6 is a perspective cut-away view of one of the illustrative lead connector sub-assemblies shown in FIG. 5.

FIG. 4 is a perspective schematic diagram view of an illustrative lead connector 105. FIG. 5 is a perspective cut-away view of the illustrative lead connector 105 shown in FIG. 4. FIG. 6 is a perspective cut-away view of one of the illustrative lead connector sub-assemblies shown in FIG. 5.

The lead connector 105 includes one or more electrically conducting contact rings 130 spaced apart by electrically insulating ring 140 and in axial alignment. An interface bond on an atomic level joins the electrically insulating ring 140 to the electrical contact ring 130. As illustrated, the electrically insulating ring 140 is joined (via a diffusion bond) between two electrical contact rings 130, 130'. These two electrical contact rings 130, 130' can also be referred to as an electrical contact ring 130 and an electrical spacer ring 130'. These three elements (two electrical contact rings 130, 130' and the electrically insulating ring 140) form a subassembly 106 that can be welded together at abutting electrical contacts 130, 130' to form the lead connector 105.

The one or more electrically conducting contact rings 130, 130' can be formed as a single element (not shown) or can include another electrically conducting contact ring that can be welded to the electrically conducting contact ring 130 to form the one or more electrically conducting contact rings 130, 130' as illustrated in the sub-assembly manufacture process described herein.

The one or more electrically conducting contact rings 130, 130' are in electrical communication with the electronics 23 and the lead connector 105 provides a hermetic seal between the sealed housing 109 interior and the lead aperture 165. The electronics 23 generally control the active medical device 102. The power source 21 can be any useful battery or power source such as an inductive coil. In some embodiments, the electronics 23 includes memory. The memory can be any magnetic, electronic, or optical media, such as random access memory (RAM), read-only memory (ROM), electronically-erasable programmable ROM, flash memory, or the like.

The one or more electrically conducting contact rings 130, 130' can be formed of any useful electrically conductive material. In many embodiments, the one or more electrically conducting contact rings 130, 130' are formed of a metallic material such as, for example, titanium, stainless steel, MP35N, niobium, tantalum, platinum, and alloys or combinations thereof. In some embodiments, the one or more electrically conducting contact rings 130, 130' are formed of a metallic material such as, for example, titanium or titanium alloy.

The electrically insulating ring 140 can be formed of any useful electrically insulating material. In many embodiments the electrically insulating ring 140 is formed of ceramic or sapphire. In some embodiments the electrically insulating ring 140 is formed of polycrystalline aluminum oxide. In some embodiments a metalization layer 141, 142 is sputter coated (for example) on the electrically insulating ring 140 to assist the formation of the diffusion bond. The metalization layer 141, 142 can be formed of any useful material. In some embodiments, the metalization layer 141, 142 is formed of niobium, rhodium, hafnium or tantalum, titanium and platinum. In some embodiments a metalization layer 141, 142 includes niobium, platinum, titanium or combinations thereof. The metalization layer 141, 142 can have any useful thickness. In some embodiments, the metalization layer 141, 142 has a thickness of less than 3 micrometer or is in a range from 10 nanometers to 1 micrometer. In many embodiments the metalization layer 141, 142 covers only a portion of the electrically insulating ring 140, specifically at the diffusion bond interface. In some embodiments the metalization layer 141, 142 is sputter coated (for example) on the electrically conducting contact rings 130, 130' in addition to or instead of the electrically insulating ring 140.

In some embodiments, the electrically conducting contact rings 130, 130' are formed of titanium and the electrically insulating ring 140 is formed of ceramic or sapphire. These elements can be joined via diffusion bonding at a temperature that is less than the phase transition temperature of titanium. For example, the elements can be placed under pressure of 1-5 MPa and processed at a temperature in a range from 800 to 1000 degrees centigrade or in a range from 850 to 950 degrees centigrade. These temperatures are less than the melting point of gold, for example. Also the pitch between electrical contact portions 130 or contact coils 150 can be reduced to 0.085 inch or less. Diffusion bonding can also improve the process control and reduce pitch variation as compared to other joining techniques.

In some embodiments, a filtering capacitor is disposed between the electrically conducting contact rings 130, 130' and the electronics 23. The filtering capacitor can effectively filter out undesirable electromagnetic interference (EMI) from the active medical device 102.

The implantable active medical device described herein can eliminate the need for a conventional separate feedthrough block that electrically connects a conventional lead connector block with the hermetically sealed electronics of the implantable active medical device. By placing the lead connector within the hermetically sealed active medical device housing, a direct electrical connection between the lead connector and the electronics can be made (as illustrated in FIG. 2). In addition, combining the feedthroughs and the external connector into a single component can reduce the size and volume of the implantable medical device and can also reduce the number of parts and connections needed to assemble the implantable active medical device.

The illustrated lead connector 105 is an elongate member extending between a lead aperture 165, first open end 166, and end cap 145, and having an inner surface defining an open lumen lead aperture 165. In some embodiments the lead connector 105 is an elongate member extending between a lead aperture 165, first open end 166 and second open end (not shown). The open lumen lead aperture 165 or lead receptacle 165 is configured to accept a lead or lead extension, as described above, and electrically couple one or more lead contacts with one or more connector contacts 130, 130' that form the elongate body of the lead connector 105, that in many embodiments is generally cylindrical.

In many embodiments, the lead aperture 165 is a cylindrical open lumen of generally circular cross-sectional area formed by an inner surface of the electrically conducting rings 130, 130' and electrically insulating rings 140 diffusion bonded together in axial alignment. The lead connector 105 defines a lead connector outer surface 170 and at least a portion of the lead connector outer surface 170 is disposed within the sealed housing 109 interior. In many embodiments, at least a majority of the lead connector outer surface 170 is disposed within the sealed housing 109 interior. In many embodiments, substantially the entire lead connector outer surface 170 is disposed within the sealed housing 109 interior and at least partially defines the sealed housing 109 interior. In some embodiments, the entire lead connector outer surface 170 is disposed within the sealed housing 109 interior.

The one or more electrically conducting contact rings 130, 130' can include one or more additional contact elements in electrical contact with and optionally disposed within each of the one or more electrically conducting contact rings 130, 130'. These one or more additional contact elements are configured to provide electrical communication between one or more electrically conducting contact rings 130, 130' and a lead contact received within the lead aperture 165. In many embodiments, these contact elements are electrically conductive and resilient to provide an interference fit between the electrically conducting contact ring 130, 130' and lead contact received within the lead aperture 165.

Examples of contact elements include, but are not limited to, spring elements. In many embodiments, the contact element includes an annular helical coil 150 (i.e., continuous coil spring 150) is disposed adjacent an inner surface of the electrically conducting contact ring 130 and/or 130, 130'. The helical annular coil 150 can be formed of any useful electrically conductive material such as, for example, a metal like gold, silver, titanium and the like. When a lead is inserted into the lead aperture 165, the lead and lead contact(s) can deflect the annular helical coil 150 and form an electrical contact between the lead contact and the electrically conducting contact ring 130. The continuous coil spring 150 provides a frictional electrical and mechanical engagement with a lead contact and the adjacent electrically conducting contact ring 130.

A mounting flange 160 can be fixed to the lead connector 105 adjacent the open end 166. The mounting flange 160 can be brazed or welded, for example to the hermetically sealed housing 109. In some embodiments, the mounting flange 160 is brazed or welded to an exterior surface of the hermetically sealed housing 109. In other embodiments, the mounting flanges 160 are brazed or welded to an interior surface of the hermetically sealed housing 109. A retention member (not shown) such as for example, a set screw, can be disposed on the lead connector 105 adjacent to the open end 166 and can assist in mechanical retention of the lead disposed within the lead aperture 165.

The lead connector 105 can be formed by any useful method. In many embodiments, the lead connector 105 is formed by assembling two or more lead connector subassemblies 106, described above. FIG. 6 is a cut-away perspective of the illustrative subassembly 106 shown in FIG. 4. Each lead connector subassembly 106 can be arranged in axial alignment and bonded utilizing a metal-to-metal bonding technique such as, laser welding or diffusion bonding, for example, to form the lead connector 105.

Each lead connector subassembly 106 includes the electrically insulating ring 140 fixed between the electrically conducting contact ring 130 and an attachment ring or electrically conducting spacer ring 130' via diffusion bonding. Thus, the electrically conducting spacer ring 130' is diffusion bonded to a first side of the electrically insulating ring 140 and the electrically conducting contact ring 130 is diffusion bonded to a second opposing side of the electrically insulating ceramic ring 140. The diffusion bond provides the hermetic seal between the between the sealed housing interior/lead connector outer surface 170 and the lead aperture 165. In some embodiments, the subassembly 106 includes a wiper seal 178 that can assist in electrical isolation of adjacent electrical contacts and also to mitigate fluid transmission within the lead aperture.

Figure 7:
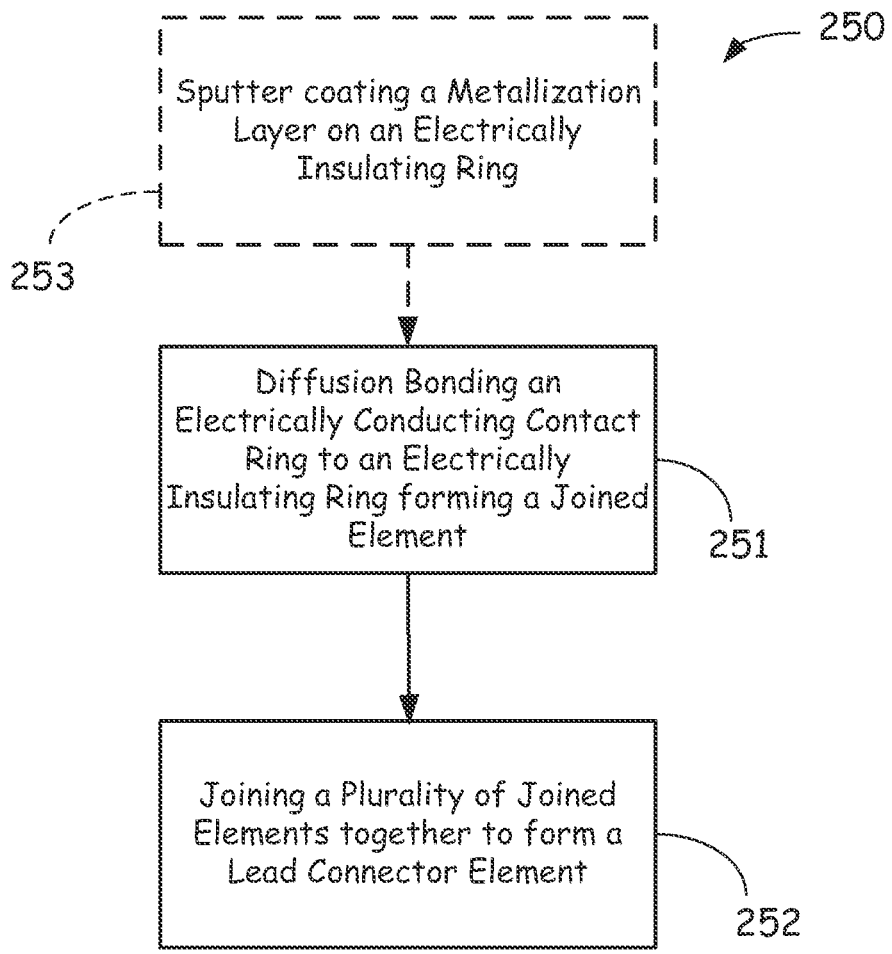
FIG. 7 is a flow diagram of an illustrative method of making a lead connector element.

FIG. 7 is a flow diagram of an illustrative method 250 of making a lead connector element. The method includes diffusion bonding an electrically conducting contact ring to an electrically insulating ring to form a joined element at block 251. A plurality of joined elements are then joined together to form the lead connector element at block 252. The electrically insulating ring can optionally be sputter coated to form a metalization layer prior to the diffusion bonding.

Thus, embodiments of the DIFFUSION BONDED LEAD CONNECTOR are disclosed. The implementations described above and other implementations are within the scope of the following claims. One skilled in the art will appreciate that the present disclosure can be practiced with embodiments other than those disclosed. The disclosed embodiments are presented for purposes of illustration and not limitation, and the present invention is limited only by the claims that follow.

What is claimed is:

1. A medical device lead connector comprising:
   electrically conducting contact rings spaced apart by an electrically insulating ring and in axial alignment, the electrically conducting contact ring and the insulating ring having an interface bond on an atomic level, a metallization layer disposed on the electrically insulating ring at the interface bond, the metallization layer having a thickness in a range from 10 nanometers to less than 1 micrometer.

2. A medical device lead connector according to claim 1, wherein the lead connector comprises a plurality of ring subassemblies fixed in axial alignment and each ring subassembly comprises an electrically insulating ring between an electrically conducting contact ring and an electrically conducting spacer ring bonded together with an interface bond on an atomic level.

3. A medical device lead connector according to claim 2, wherein adjacent ring subassemblies are welded together to form a rigid medical device lead connector.

4. A medical device lead connector according to claim 1, wherein the interface bond on an atomic level is a diffusion bond.

5. A medical device lead connector according to claim 4, wherein the electrically conducting contact ring comprises titanium or titanium alloys and the electrically insulating ring comprises sapphire or a ceramic material.

6. A medical device lead connector according to claim 1, wherein the metallization layer comprises niobium, platinum, titanium or combinations thereof.

7. A medical device lead connector according to claim 1, wherein the metallization layer covers only a portion of the electrically insulating ring at an interface of the diffusion bond.

8. An implantable medical device comprising;
a hermetically sealed housing defining a sealed housing interior;
a power source and electronics in electrical communication and disposed within the sealed housing interior; and
a lead connector projecting into the sealed housing interior and having an outer surface, and an inner surface defining a lead aperture, the lead connector comprising one or more electrically conducting contact rings spaced apart by electrically insulating rings and joined together with a diffusion bond, a metallization layer disposed on the electrically insulating ring at the diffusion bond, the metallization layer having a thickness in a range from 10 nanometers to less than 1 micrometer, the one or more electrically conducting contact rings in electrical communication with the electronics, and the diffusion bond providing a hermetic seal between the lead connector outer surface and the lead connector inner surface.

9. An implantable medical device according to claim 8, wherein the lead connector comprises a plurality of ring subassemblies fixed in axial alignment, each ring subassembly comprises the diffusion bond fixing an electrically insulating ring between an electrically conducting contact ring and an electrically conducting spacer ring.

10. An implantable medical device according to claim 9, wherein the diffusion bond directly bonds the electrically conducting contact ring and the electrically conducting spacer ring with the electrically insulating ring via the metallization layer.

11. An implantable medical device according to claim 10, wherein the electrically conducting contact ring comprises titanium or titanium alloys and the electrically insulating ring comprises sapphire or a ceramic material.

12. An implantable medical device according to claim 9, wherein adjacent ring subassemblies are welded together for form a rigid lead connector.

13. An implantable medical device according to claim 8, wherein the metallization layer comprises niobium, platinum, titanium or combinations thereof.

14. An implantable medical device according to claim 8, wherein the metallization layer covers a portion of the electrically insulating ring at an interface of the diffusion bond.

15. A lead connector formed by the process of:
sputtering a metallization layer that has a thickness in a range from 10 nanometers to less than 1 micrometer onto only a diffusion bond area portion of an electrically insulating ring;
diffusion bonding the electrically insulating ring between a first electrically conducting contact ring and a second electrically conducting contact ring to form an aligned joined element; and
joining a plurality of aligned joined elements in axial alignment to form a lead connector having a lead aperture.

16. The lead connector according to claim 15, wherein the electrically conducting contact ring comprises titanium or titanium alloys and the electrically insulating ring comprises sapphire or a ceramic material.

17. The lead connector according to claim 15, wherein the metallization layer comprises niobium, platinum, titanium or combinations thereof.

* * * * *